United States Patent
Moshiree et al.

(10) Patent No.: US 11,064,905 B2
(45) Date of Patent: Jul. 20, 2021

(54) INGESTIBLE CAPSULE DEVICE FOR COLLECTING FLUID ASPIRATES

(71) Applicant: UNIVERSITY OF MIAMI, Miami, FL (US)

(72) Inventors: Baharak Moshiree, Charlotte, NC (US); Alex Espinosa, Miami, FL (US)

(73) Assignee: UNIVERSITY OF MIAMI, Miami, FL (US)

( * ) Notice: Subject to any disclaimer, the term of this patent is extended or adjusted under 35 U.S.C. 154(b) by 504 days.

(21) Appl. No.: 16/082,009

(22) PCT Filed: Mar. 3, 2017

(86) PCT No.: PCT/US2017/020728
§ 371 (c)(1),
(2) Date: Sep. 4, 2018

(87) PCT Pub. No.: WO2017/152093
PCT Pub. Date: Sep. 8, 2017

(65) Prior Publication Data
US 2018/0368730 A1      Dec. 27, 2018

Related U.S. Application Data

(60) Provisional application No. 62/303,917, filed on Mar. 4, 2016.

(51) Int. Cl.
  *A61B 5/145*   (2006.01)
  *A61B 5/07*    (2006.01)
  *A61B 10/00*   (2006.01)
(52) U.S. Cl.
  CPC ............ *A61B 5/073* (2013.01); *A61B 5/1451* (2013.01); *A61B 5/14539* (2013.01);
  (Continued)

(58) Field of Classification Search
  CPC ... A61B 5/073; A61B 5/1451; A61B 10/0045; A61B 5/14539; A61B 5/14546; A61B 2010/0061
  See application file for complete search history.

(56) References Cited

U.S. PATENT DOCUMENTS

| 5,395,366 A | 3/1995 | D'Andrea et al. |
| 7,914,442 B1 * | 3/2011 | Gazdzinski .......... A61B 5/0071 600/109 |

(Continued)

OTHER PUBLICATIONS

International Search Report and Written Opinion for Application No. PCT/US17/20728, dated Jul. 20, 2017.

(Continued)

*Primary Examiner* — Navin Natnithithadha
(74) *Attorney, Agent, or Firm* — Marshall, Gerstein & Borun LLP

(57) ABSTRACT

An ingestible capsule device collects fluid aspirates from locations within the body, locations such as the small intestine, and retains the fluid aspirates free from contamination as the capsule device is expelled from the body. The device allows for microbial and metabolomics analysis for a variety of gastrointestinal, allergic, endocrinologic, and oncologic diseases. In some examples, the capsule device is a multi-stroke device that includes a capsule shell and two reservoirs located within the shell. Check valves work in conjunction with a vacuum pressure pumping mechanism to control fluid movement from one reservoir to another, where one of the reservoirs may be expandable and permeable to some fluids. In other examples, the capsule device employs a peristaltic pump fluid control with the capsule device, and a single semi-permeable bladder stores collected fluid aspirate.

22 Claims, 11 Drawing Sheets

(52) U.S. Cl.
CPC ...... *A61B 10/0045* (2013.01); *A61B 5/14546* (2013.01); *A61B 2010/0061* (2013.01)

(56) References Cited

U.S. PATENT DOCUMENTS

| | | | |
|---|---|---|---|
| 8,068,897 B1* | 11/2011 | Gazdzinski | A61B 1/00156 |
| | | | 600/476 |
| 9,227,011 B2* | 1/2016 | Shimizu | A61M 5/1723 |
| 2007/0173738 A1 | 7/2007 | Stoltz | |
| 2008/0194912 A1 | 8/2008 | Trovato et al. | |
| 2011/0106063 A1 | 5/2011 | Dijksman et al. | |
| 2012/0071710 A1* | 3/2012 | Gazdzinski | A61B 1/0002 |
| | | | 600/101 |
| 2014/0275860 A1 | 9/2014 | Rottenberg et al. | |
| 2015/0157838 A1* | 6/2015 | Gazdzinski | A61B 1/043 |
| | | | 600/3 |

OTHER PUBLICATIONS

International Preliminary Report on Patentability for Application No. PCT/US17/20728, dated Sep. 4, 2018.

* cited by examiner

INGESTIBLE CAPSULE DEVICE FOR COLLECTING FLUID ASPIRATES

CROSS-REFERENCE TO RELATED APPLICATION

This is a US national stage of International Application No. PCT/US2017/020728, filed Mar. 3, 2017, which claims the priority of U.S. Provisional Patent Application No. 62/303,917, filed Mar. 4, 2016, and entitled "Ingestible Capsule Device for Collecting Fluid Aspirates"; the entire contents thereof are incorporated by reference herein.

FIELD OF THE DISCLOSURE

This disclosure relates generally to an ingestible capsule device, and more specifically, to an ingestible capsule device capable of collecting fluid aspirates from the small intestine for microbial and metabolite composition analysis.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Disturbances in the homeostasis of the gastrointestinal (GI) tract's microbiome, called intestinal dysbiosis, is associated with many diseases such as diabetes, obesity, colon cancer, inflammatory bowel diseases such as Crohn's disease and irritable bowel syndrome (IBS). Traditionally, information about specifically the small intestine's microbiome has been collected in one of two ways. First, a catheter may be introduced into a patient via a fiberoptic endoscope advanced to the small intestine to collect fluid if fluid is present. This method is invasive and presents a number of risks, namely the risk of perforation from insertion of the endoscope, the risk of the introduction of infection by the endoscope itself, the risk of bleeding, the risks of sedation, and the risk of contamination by fluid aspirated from other portions of the digestive track through which the catheter travels, such as the mouth which is often full of oral bacteria. Alternatively, a less accurate noninvasive test which is noninvasive can be performed via a hydrogen breath test to indirectly detect the end products of bacteria via assessment of $CO_2$ and methane production by bacteria. However, the breath test does not enable identification of the actual pathogenic bacteria in the small intestine, which is sometimes necessary for proper antibiotic treatment. This test is commonly performed in patients who complain of abdominal pain, bloating, diarrhea and otherwise unexplained chronic gastrointestinal symptoms.

Ingestible capsule devices have previously been developed for drug delivery purposes. However, such capsule devices do not provide a means by which to gather fluid aspirates from the small intestine or other locations within the body. Moreover, with conventional ingestible devices, keeping collected fluid aspirates free from contamination (e.g., as the capsule device is expelled from the body) is a challenge. Gathering fluid aspirates from the small intestine is particularly challenging, because the small intestine is filled with air along with the fluid aspirates. As a result, a capsule device may suction air instead of or in addition to fluid aspirate depending on the position of the capsule device within the small intestine.

SUMMARY OF THE DISCLOSURE

The current disclosure is directed to multiple embodiments of an ingestible capsule device that can collect fluid aspirates from locations within the body such as the small intestine and keep the fluid aspirates free from contamination from the mouth or colon as the capsule device is expelled from the body. To achieve these ends, in some embodiments, the capsule device has a multi-stroke intake process. The capsule device includes a capsule shell and has two reservoirs located within the shell. The capsule shell has an inlet for receiving fluid that is connected to the first reservoir. A first check valve located between the inlet and the first reservoir controllably passes fluid into the first reservoir during an intake stroke in response to actuation by a vacuum pressure pumping mechanism in the capsule device. The second reservoir is in fluid communication with the first reservoir through a second check valve configured to pass fluid accumulated in the first reservoir, over one or more intake strokes, into the second reservoir during an exhaust stroke and in response to actuation by the vacuum pressure pumping mechanism. The first check valve and the second check valve are simultaneously controlled by the vacuum pressure pumping mechanism to block fluid from passing from the second reservoir into the first reservoir during operation of the capsule device, thus ensuring that the fluid aspirates gathered by the capsule device do not become contaminated as the capsule device is expelled from a patient's body.

In some multi-stroke embodiments within the scope of the present disclosure, the second reservoir is expandable within the capsule shell and is also expandable outside the capsule if, for example, a portion of the capsule shell is digestible. For example, the second reservoir may have a receiving end adjacent the first reservoir and configured such that the receiving end is maintained in a fixed position relative to the first reservoir and a distal end expandable in response to increases in fluid in the second reservoir. The second reservoir may be a bellows. The maximum volume of the second reservoir may be equal to or greater than one cubic centimeter.

Because air may sometimes be taken in during the intake process of the capsule device, in some multi-stroke embodiments within the scope of the present disclosure, the second reservoir of the capsule device is permeable to some fluids. This allows air, for example, to exit the second reservoir, providing more space for desired fluids such as fluid aspirate from the small intestine. In some multi-stroke embodiments within the scope of the present disclosure, the second reservoir may be a bellows made from an electrospun polymer that is permeable to some fluids.

The vacuum pressure pumping mechanism of a multi-stroke device may include a diaphragm providing a movable casing for the first reservoir. The diaphragm may be controllably moved between an intake stroke position and an exhaust stroke position by a magnetic solenoid driver. The vacuum pressure pumping mechanism may include a spring or a gear mechanism, and the diaphragm may be bistable.

In other embodiments within the scope of the present disclosure, a positive displacement pumping device may be used, e.g., having a peristaltic pumping mechanism that collects fluid from within the body. In such examples, in place of the two reservoirs, the capsule device may be implemented with a single reservoir, within a shell for storing the fluid aspirate. The peristaltic pump may be driven by a high rotation rate motor (mini-motor), capable of rotating of 10,000, 20,000, 30,000 to 40,000 rotations per minute, by way of example. The peristaltic pump rotates at a lower rotation rate, determined by a gear ratio, and may continuously receive fluid collected from an inlet hole and aspirate that fluid into the collection reservoir.

The capsule device may include a non-dissolvable cap that houses the peristaltic pump, which may be mounted on a universal mount. An inlet conduit of the peristaltic pump may extend through the inlet hole in the non-dissolvable cap, and an outlet conduit of the peristaltic pump may extend through an outlet hole in the universal mount. The outlet conduit may extend into a single permeable bladder. The permeable bladder may be extendable, in some embodiments doubling or tripling in size, between an initial size and fluid-filled size. A dissolvable cap may cover the permeable bladder. The non-dissolvable cap and the dissolvable cap may be configured such that together they form a shell that can easily be swallowed. The dissolvable cap may be ejected several minutes after swallowing during transit through the patient's body by the expansion of the permeable bladder. The semi-permeable bladder may be separable from the mount and may include a bladder seal to close the semi-permeable bladder upon removal of the outlet conduit.

The peristaltic pump in the capsule device includes a stator with a central aperture with a notched edge. A cycloid gear engages the stator. An eccentric or cam-shaped crank is connected to the center of the cycloid gear. A stator cover covers the stator and cycloid gear, and an output disk is connected outside the stator cover to the eccentric crank. Output pins extend from the output disk and are connected to rollers. A media tubing is secured in an arc-configuration by the stator cover. As the eccentric crank turns, the rollers are alternately engaged and disengaged with the media tubing. When engaged with the media tubing, the rollers pinch the media tubing closed, thus forcing fluid within the media tubing to move through the media tubing. When the rollers disengage the media tubing, fluid flow is induced by the newly created vacuum to flow through the media tubing. The media tubing may be configured to overlap for a distance, and the peristaltic pump may be sealed by stopping a roller within the distance where the media tubing overlaps.

In both multi-stroke and peristaltic pump embodiments within the scope of the present disclosure, the capsule device may include a controller connected to a battery and to the pumping mechanism. The controller comprises at least one computer processor and at least one memory storing computer-readable instruction (e.g., program) that when executed causes the processor to perform the various control functions described herein. The controller may have a number of programs to ensure proper collection of fluid aspirates. For example, in multi-stroke embodiments, the controller may have a collection mode program that, when activated, causes the vacuum pressure pumping mechanism to move continuously between the intake stroke and the exhaust stroke, opens the first check valve and closes the second check valve during the intake stroke, and closes the first check valve and opens the second check valve during the exhaust stroke. In multi-stroke embodiments, the controller may have a contamination resistance mode program that, when activated, closes the first check valve, closes the second check valve, and stops movement of the vacuum pressure pumping mechanism. In embodiments that are not multi-stroke, the controller may simply have a collection mode program and off mode program with the peristaltic pump running during the collection mode program and turned off during the off mode program. The collection mode program may run for a set period of time, may run multiple times, and may run multiple times at predetermined intervals.

The collection mode program may be connected to a timer, and the timer may activate the collection mode program. Alternately, the controller may be connected to a sensor disposed on the capsule shell or non-dissolvable cap, and a condition sensed by the sensor may activate the collection mode program. For example, the pH level within the human digestive track changes depending on the organ, with the small intestine generally having a pH range of 5.5 to 8.0. The sensor may be a pH sensor, and the condition sensed by the sensor to activate the collection mode may be a specific pH range such as 5.5 to 8.0. The pH in the stomach usually ranges between 1 and 4 and the pH in the colon is less than 5.5. The motor controller may monitor the current drawn from the motor and identify periods when a greater amount of current is drawn and periods when a lesser amount of current is drawn within a cycle of a peristaltic pump, and the collection mode program may wait for a period when a greater amount of current is drawn to end the collection mode program as this may indicate that a roller is within a distance of overlapping media tubing, thereby sealing the peristaltic pump.

In some embodiments within the scope of the present disclosure, the controller includes a wireless receiver, and the capsule device includes a remote wireless transmitter. In multi-stroke embodiments, the wireless receiver may receive from the remote wireless transmitter a signal that activates the controller to initiate an intake stroke, initiate an exhaust stroke, open or close the first check valve, and open or close the second check valve. In both multi-stroke and non-multi-stroke embodiments, the wireless receiver may receive from the remote wireless transmitter a signal to active the collection mode program. In multi-stroke embodiments, the wireless receiver may receive from the remote wireless transmitter a signal to activate the contamination resistance mode program. Alternately, the contamination resistance mode program may be activated by cessation of the collection mode program. In peristaltic pump embodiments, the wireless receiver may receive from the remote wireless transmitter a signal that either starts or stops the running of the control motor and the peristaltic pump. Peristaltic pump embodiments may further include a sample dispensation mode. In sample dispensation mode, the action of the peristaltic pump may be reversed to dispense the collected sample.

DETAILED DESCRIPTION

Figure 1:
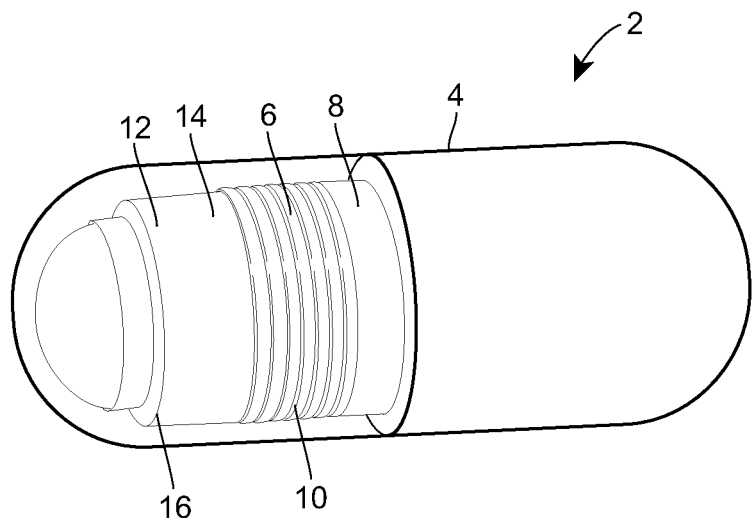
FIG. 1 illustrates an isometric view of a multi-stroke capsule device of the present disclosure with a capsule shell in a closed position.

FIG. 1 illustrates a multi-stroke capsule device 2 of the present disclosure. The capsule device 2 has a capsule shell 4 surrounding a vacuum pressure pumping mechanism 6. In the embodiment depicted in FIG. 1, the vacuum pressure pumping mechanism 6 includes a diaphragm 8 connected to an actuator coil 10. A controller 12 and a battery 14 are in communication with the actuator coil 10 and are contained within an enclosure 16 in the capsule shell 4.

Figure 2:
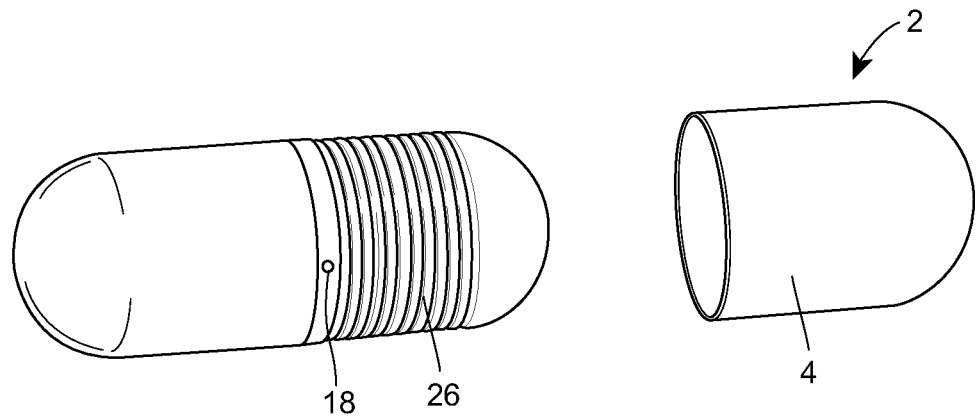
FIG. 2 illustrates an isometric view of a multi-stroke capsule device of the present disclosure with a capsule shell in an open position.

FIG. 2 illustrates a multi-stroke capsule device 2 of the present disclosure with a capsule shell 4 in an open position. An inlet 18 of the multi-stroke capsule device 2 is visible. In the embodiment depicted in FIG. 2, a second reservoir 26 is expandable and the outside of the second reservoir 26 is visible.

Figure 3A:
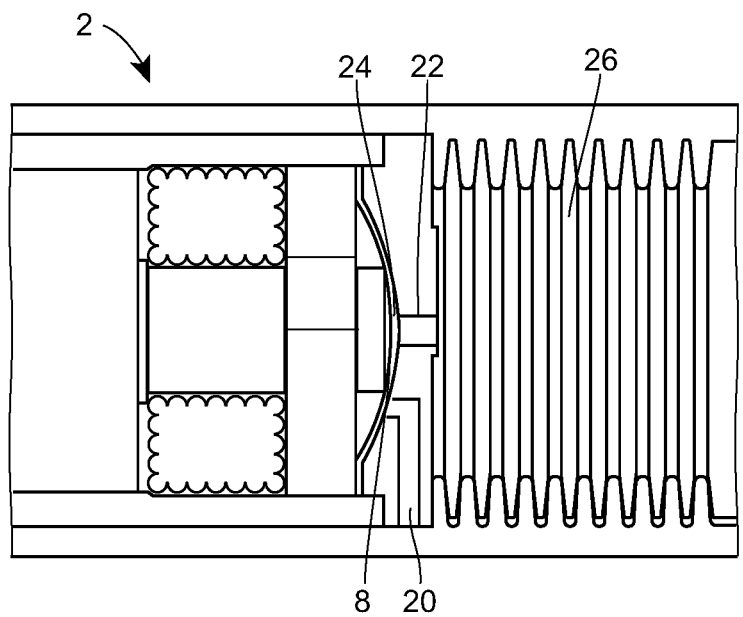
FIG. 3A illustrates a cross-sectional view of a multi-stroke capsule device of the present disclosure during an intake stroke when the diaphragm is closed and the first check valve and second check valve are closed.

FIGS. 3A-3D illustrate the intake stroke of a multi-stroke collection mode program carried out by the multi-stroke capsule device 2. FIG. 3A illustrates the multi-stroke capsule device 2 of the present disclosure during an intake stroke when the diaphragm 8 is closed and the first check valve 20 and second check valve 22 are closed. No fluid is located in the first reservoir 24 or the second reservoir 26.

Figure 3B:
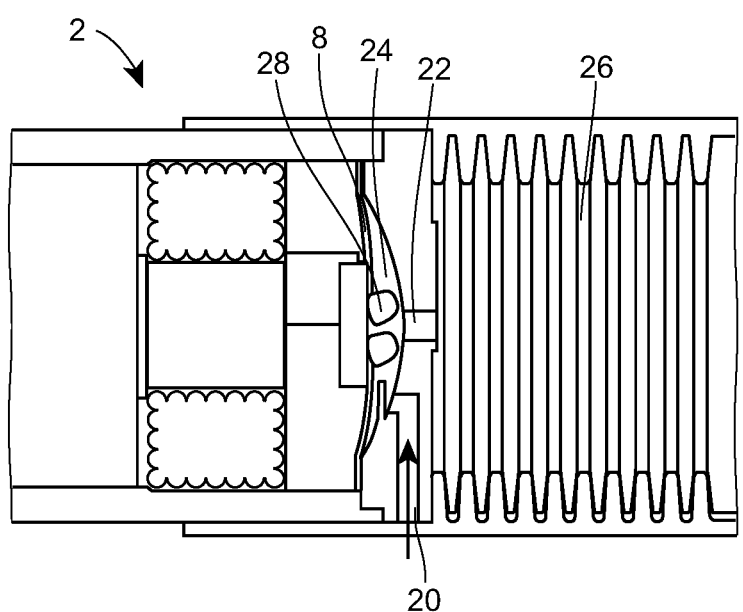
FIG. 3B illustrates a cross-sectional view of a multi-stroke capsule device of the present disclosure during an intake stroke when the diaphragm is opening and the first check valve is opening.

FIG. 3B illustrates the multi-stroke capsule device 2 of the present disclosure during an intake stroke when the diaphragm 8 is opening and the first check valve 20 is opening. Fluid aspirate 28 enters (see, inlet and arrow) the first reservoir 24 through the first check valve 20. The second check valve 22 is still closed, and no fluid aspirate 28 is able to enter the second reservoir 26.

Figure 3C:
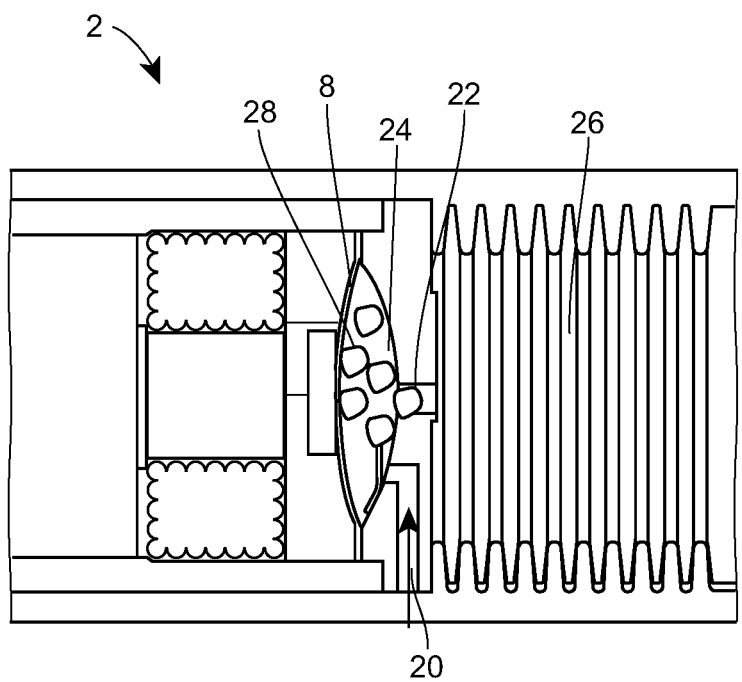
FIG. 3C illustrates a cross-sectional view of a multi-stroke capsule device of the present disclosure during an intake stroke when the diaphragm is open and the first check valve is open.

FIG. 3C illustrates the multi-stroke capsule device 2 of the present disclosure during an intake stroke when the diaphragm 8 is deflected to receiver the aspirate 28 and when the first check valve 20 is open. Fluid aspirate 28 fills the first reservoir 24 through the first check valve 20. The second check valve 22 is still closed, and no fluid aspirate 28 is entering the second reservoir 26.

Figure 3D:
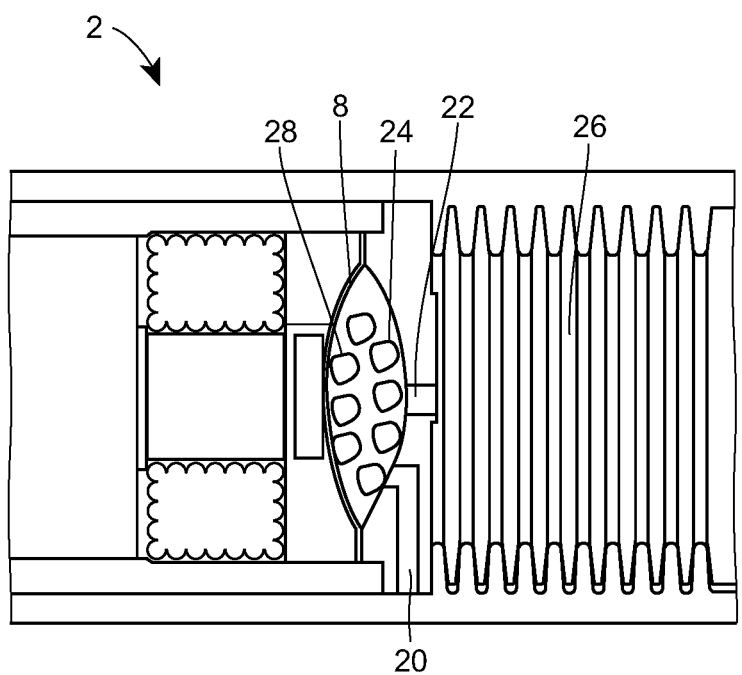
FIG. 3D illustrates a cross-sectional view of a multi-stroke capsule device of the present disclosure during an intake stroke when the diaphragm is open and the first check valve is again closed.

FIG. 3D illustrates the multi-stroke capsule device 2 of the present disclosure at the end of an intake stroke when the diaphragm 8 is fully deflected (also termed fully opened) and the first check valve 20 is again closed. Fluid aspirate 28 fills the first reservoir 24. The second check valve 22 is still closed, and no fluid aspirate 28 is entering the second reservoir 26.

In the illustrated example, the diaphragm 8 moves between the closed and fully open position using a control mechanism, in particular a magnetic solenoid driver having a magnetic member mounted to a back surface of the diaphragm 8 and attracted and repelled in response to control from a fixed magnetic member surrounded by the coil spring controlling the generated magnetic field to selectively alternate between an intake stroke and an exhaust stroke. Thus, in some examples, the control mechanism may be a vacuum pressure pumping mechanism that includes the diaphragm 8 providing a movable casing for the first reservoir 24. In some examples, this vacuum pressure pumping mechanism uses a gear mechanism, an example of which is discussed further below. In some examples, the vacuum pressure pumping mechanism is designed such that the diaphragm is bistable.

Figure 4A:
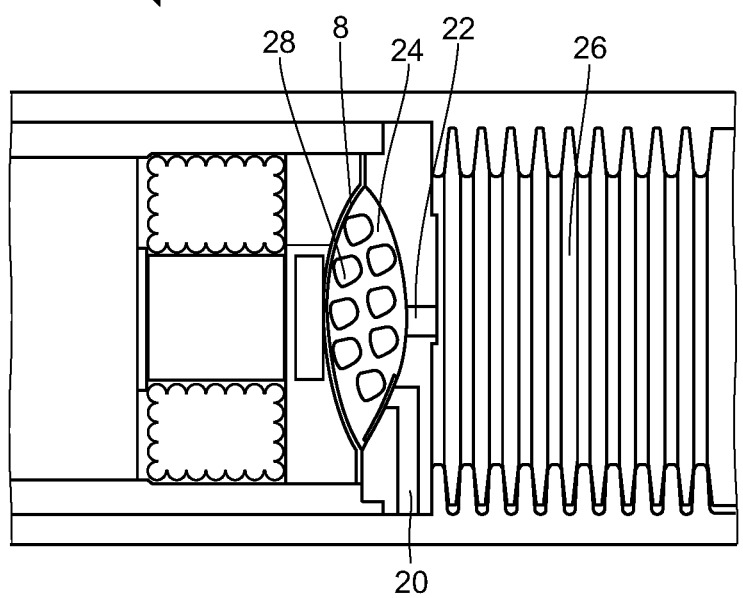
FIG. 4A illustrates a cross-sectional view of a multi-stroke capsule device of the present disclosure during an exhaust stroke when the diaphragm is open and the first check valve and the second check valve are closed.
Figure 4B:
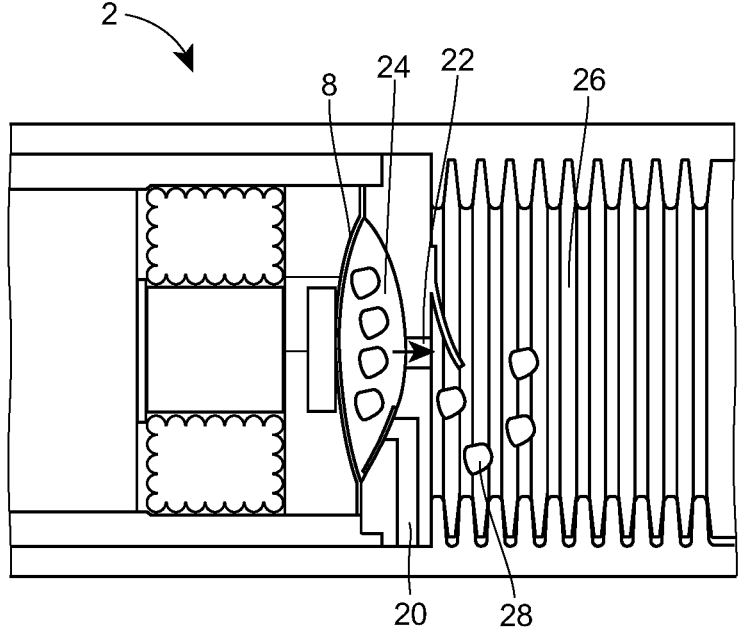
FIG. 4B illustrates a cross-sectional view of a multi-stroke capsule device of the present disclosure during an exhaust stroke when the diaphragm is closing and the second check valve is opening.

FIGS. 4A-4B illustrate the exhaust stroke of a multi-stroke collection mode program carried out by a multi-stroke capsule device 2. FIG. 4A illustrates the multi-stroke capsule device 2 of the present disclosure at the beginning of an exhaust stroke when the diaphragm 8 is open and the first check valve 20 and the second check valve 22 are closed. Because the beginning of an exhaust stroke generally occurs at the same time as the end of an intake stroke, FIGS. 3D and 4A are identical.

FIG. 4B illustrates the multi-stroke capsule device 2 of the present disclosure during an exhaust stroke when the diaphragm 8 is closing (expelling the aspirate 28) and the second check valve 22 is opening. The first check valve 20 is closed. Fluid aspirate 28 in the first reservoir 24 begins to move to the second reservoir 26 through the second check valve 22.

Figure 4C:
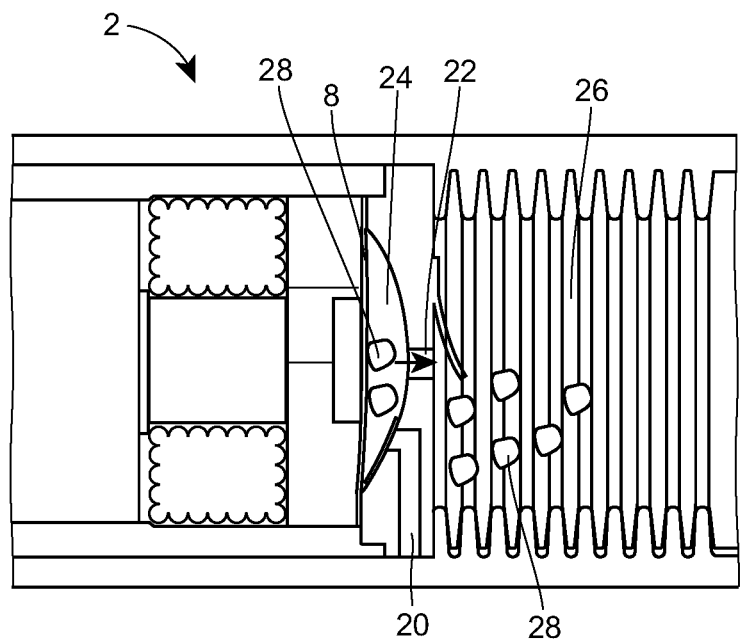
FIG. 4C illustrates a cross-sectional view of a multi-stroke capsule device of the present disclosure during an exhaust stroke when the diaphragm is closed and the second check valve is open.

FIG. 4C illustrates the multi-stroke capsule device 2 of the present disclosure during an exhaust stroke when the diaphragm 8 is closing (expelling the aspirate 28) and the second check valve 22 is open. The first check valve 20 is closed. Fluid aspirate 28 in the first reservoir 24 continues to move to the second reservoir 26 through the second check valve 22. If the second check valve 22 is expandable, the second check valve 22 may begin to expand as fluid aspirate 28 enters.

Figure 4D:
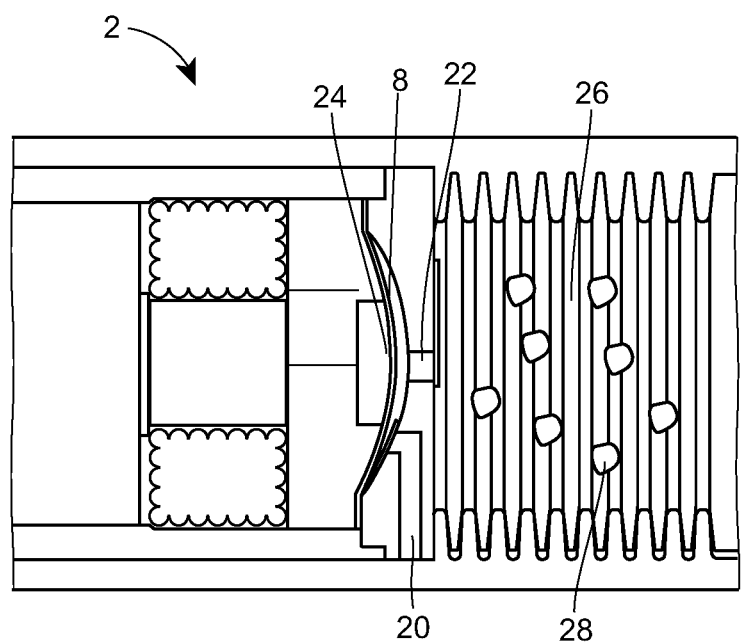
FIG. 4D illustrates a cross-sectional view of a multi-stroke capsule device of the present disclosure during an exhaust stroke when the diaphragm is closed and the second check valve is again closed.

FIG. 4D illustrates the multi-stroke capsule device 2 of the present disclosure during an exhaust stroke when the diaphragm 8 is closed (e.g., fully deflected away from the magnetic solenoid of the vacuum pumping pressure mechanism) and the second check valve 22 is again closed. The first check valve 20 is also closed. Fluid aspirate 28 has exited the first reservoir 24 and is now stored in the second reservoir 26.

Figure 5:
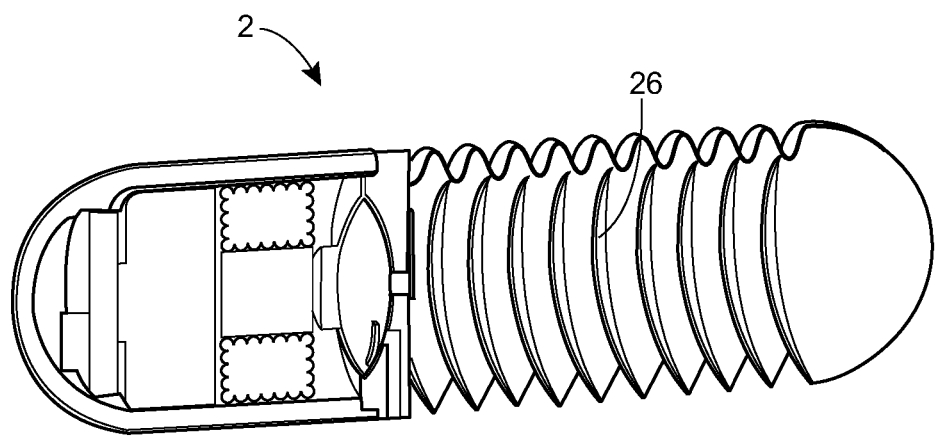
FIG. 5 illustrates an isometric view of a multi-stroke capsule device of the present disclosure when the second reservoir is expanded.

FIG. 5 illustrates the multi-stroke capsule device 2 of the present disclosure when the second reservoir 26 is expanded. The second reservoir 26 may be a bellows, and the maximum volume of the second reservoir 26 may be a cubic centimeter. In some embodiments, the second reservoir 26 may be made from a material that is permeable to some fluids, such as air. For example, the second reservoir 26 may be made from an electrospun polymer. The ability of the second reservoir 26 to expel air, through a permeable membrane, allows the volume of the second reservoir 26 to be reserved for collection of a desired fluid, such as fluid aspirates from the small intestine. As the reservoir 26 fills with fluid aspirate, air is pushed out through the membrane.

Figure 6:
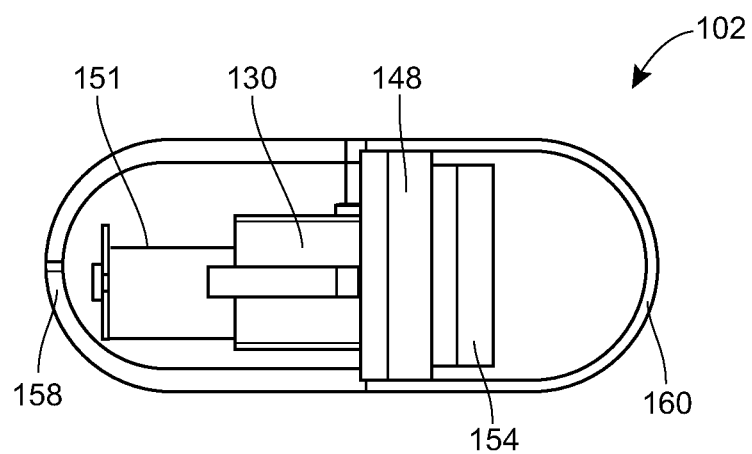
FIG. 6 illustrates a cross-sectional view of a peristaltic pump capsule device of the present disclosure.

FIG. 6 depicts a cross-section of a capsule device 102 having a peristaltic pump 130. As shown in FIGS. 6-8C, the peristaltic pump 130 is attached to a universal mount 148. Fluid aspirate is drawn into the peristaltic pump through an inlet conduit 150, travels through media tubing 144, and exits the peristaltic pump through an outlet conduit 152. A permeable bladder 154 is connected to the universal mount 148, and the outlet conduit 152 extends through an outlet hole 156 in the universal mount 148 into the permeable bladder 154. Like the second reservoir 26 discussed above, the permeable bladder 154 may be a bellows, and the maximum volume of permeable bladder 154 may be a cubic centimeter. In some embodiments, the permeable bladder 154 may be made from a material that is permeable to some fluids, such as air. For example, the permeable bladder 154 may be made from an electrospun polymer. The permeable bladder may have a receiving end adjacent universal mount and configured such that the receiving end is maintained in a fixed position relative to the universal mount and a distal end expandable in response to increases in fluid in the permeable bladder. The receiving end may be formed of a hardened material and includes a sealable connection mechanism for attaching to the universal mount 148. The expandable end is formed of an expandable material such as an electrospun polymer. The expandable material may be air permeable throughout the entire bladder 154 or only permeable over portions thereof, e.g., around the distal tip end or around the cylindrical sides of the bladder 154.

In operation, a motor 151 in the pump 130 controls operation of a peristaltic pumping mechanism (see, FIG. 8). The motor 151 includes a controller that determines the timing and operation of the pump 130. That controller, for example, may receive wireless control signals from an external transmitter indicating to start and/or stop the pump 130. An example controller is described below in reference to FIG. 11. In some examples, that controller is programmed to start and stop operation of the pump 130 at predetermined times, e.g., at a time at which point the pill should be digested into the desired location in the GI track (1 hour, 2 hours, 3 hours, 6 hours, 7 hours, etc.). In some examples, the controller is responsive to a sensor in the device 102, such as a pH sensor or impedance sensors electronically coupled to the motor 151 and controller.

In any event, as fluid is aspirated into the bladder 154 using the peristaltic pump 130, the bladder 154 fills and presses against the cap 160 and eventually, after a certain fluid volume, forces the cap 160 to fully disengage and release from the assembly. In some examples, the bladder 154 is multilayer structure, having a permeable inner expandable layer and an expandable outer layer that is not permeable. Both these layers may be retained within the cap 160. During a sample dispensation mode, the direction of the pump 130 may be reversed so that fluid aspirate collected in the bladder 154 is expelled from the capsule device 102 through the inlet conduit 150.

Figure 7:
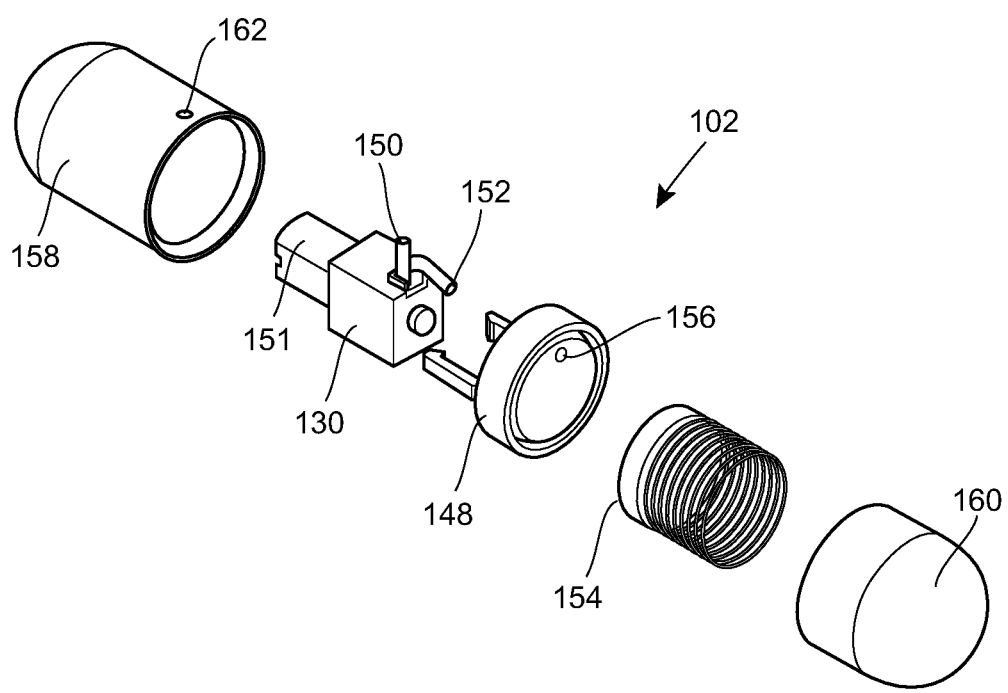
FIG. 7 illustrates an exploded view of a peristaltic pump capsule device of the present disclosure.

A non-dissolvable cap 158 may surround the peristaltic pump 130 and, in conjunction with the universal mount 148, form a shell with a dissolvable cap 160 that surrounds the permeable bladder 154. The dissolvable cap 160 may be impermeable in order to, for example, maintain the shape of the permeable bladder 154 prior to the capsule device 102 reaching the small intestine or location from which fluid is to be collected. The dissolvable cap 160 may be forced off the universal mount 148 by the permeable bladder 154 as the permeable bladder 154 fills with fluid and expands. The non-dissolvable cap 158 may include an inlet hole 162 through which the inlet conduit 150 may extend. FIG. 7 depicts the capsule device 102 shown in FIG. 6 in an expanded view.

Figure 8A:
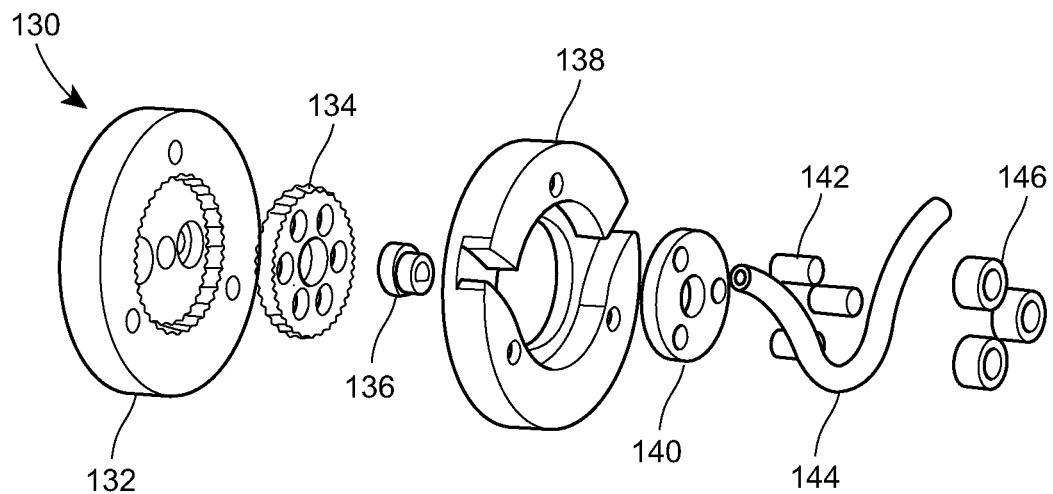
FIG. 8A illustrates an exploded isometric view of a peristaltic pump for a capsule device of the present disclosure.
Figure 8B:
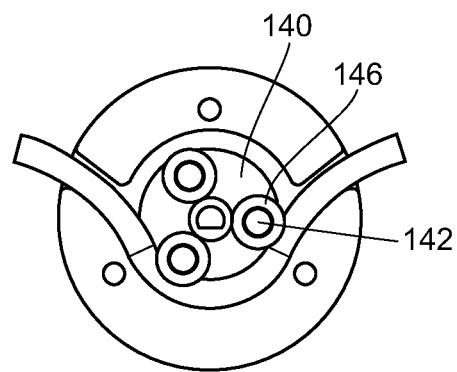
FIG. 8B illustrates a top view of the peristaltic pump illustrated in FIG. 8A.
Figure 8C:
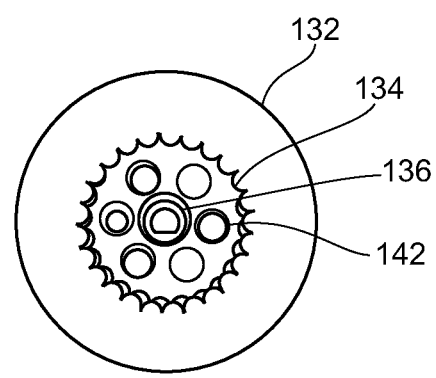
FIG. 8C illustrates a cross-sectional view of the peristaltic pump illustrated in FIG. 8A.

FIGS. 8A-8C illustrate various elements of the peristaltic pump 130 that may be used as a vacuum pressure pumping mechanism 6. FIG. 8A illustrates an exploded isometric view of the peristaltic pump 130 for a capsule device 102 of the present disclosure. The peristaltic pump 130 includes a stator 132. A cycloid gear 134 engages the stator 132. An eccentric or cam-shaped crank 136 is connected to the center of the cycloid gear 134. A stator cover 138 covers the stator 132 and cycloid gear 134, and an output disk 140 is connected outside the stator cover 138 to the eccentric crank 136. Output pins 142 extend from the output disk 140 and are connected to rollers 146. A media tubing 144 is secured in an arc-configuration by the stator cover 138. As the eccentric crank 136 turns, the rollers 146 are alternately engaged and disengaged with the media tubing 144. When engaged with the media tubing 144, the rollers 146 pinch the media tubing 144 closed, thus forcing fluid within the media tubing 144 to move through the media tubing 144. When the rollers 146 disengage the media tubing 144, fluid is induced by the newly created vacuum to flow through the media tubing 144.

FIG. 8B illustrates a top view of the peristaltic pump 130 illustrated in FIG. 8A. The output disk 140 surrounds output pins 142, which are connected to rollers 146. FIG. 8C illustrates a cross-sectional view of the peristaltic pump 130 illustrated in FIGS. 8A and 8B. The stator 132 is engaged with the cycloid gear 134. The eccentric crank 136 is centered, while the rollers 142 are located around the eccentric crank 136.

Figure 9:
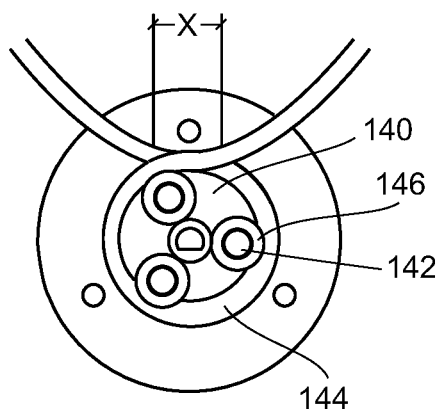
FIG. 9 illustrates an alternate arrangement of a peristaltic pump for a capsule device of the present disclosure.

FIG. 9 illustrates an alternate arrangement of the peristaltic pump 130. As in FIG. 8B, the output disk surrounds output pins 142, which are connected to rollers 146. The rollers 146 are alternately engaged and disengaged with the media tubing 144, thus forcing fluid within the media tubing 144 to move through the media tubing 144. However, in FIG. 9, the media tubing overlaps itself for a distance x. If a roller 146 is stopped within distance x, the media tubing 144 is sealed such that no fluid can enter or exit media tubing 144. The motor responsible for movement of the rollers 146, such as motor 151 in FIG. 7, draws a higher current when a roller is engaged with the overlapping portion of the media tubing within distance x. By monitoring the current drawn by the motor, a capsule device 102 can be programmed to stop the motor when a roller is within distance x, such that the media tubing 144 is sealed. For example, the capsule device 102 may run the collection mode program for a set period of time, may check the amount of current being drawn by the motor, and may stop movement of the motor when the a higher amount of current is being drawn, which indicates that media tubing 144 is sealed by a roller 146.

Figure 10A:
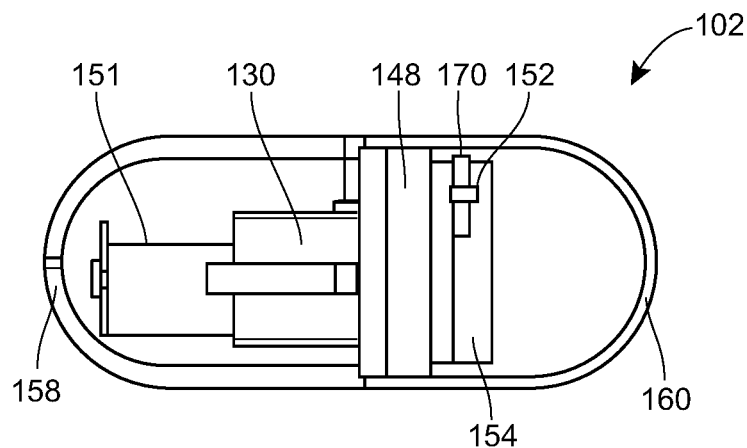
FIG. 10A illustrates a cross-sectional view of a peristaltic pump capsule device of the present disclosure adapted to split in half after completing collection of fluid aspirate.
Figure 10B:
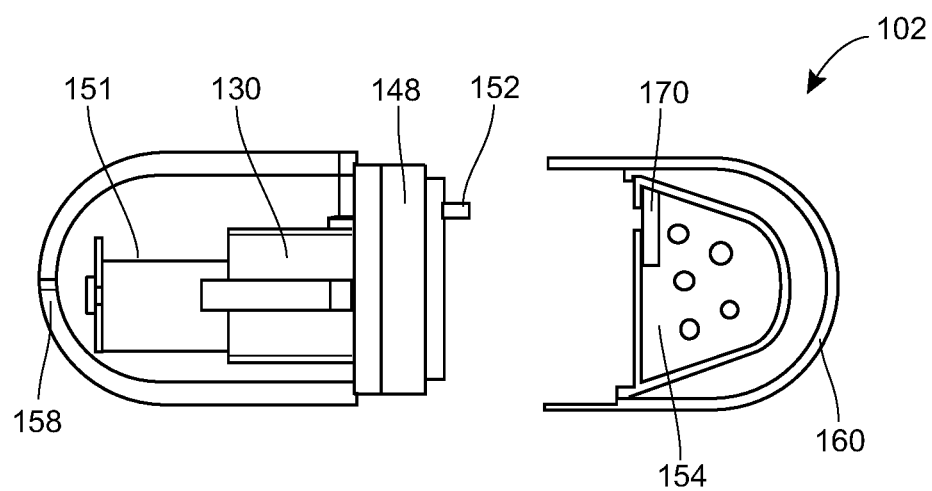
FIG. 10B illustrates a cross-sectional view of the peristaltic pump capsule device illustrated in FIG. 10A after the peristaltic pump capsule device has split in half.

FIG. 10A illustrates a cross-section of a capsule device 102 having a peristaltic pump 130 similar to that depicted in FIG. 6, except that the capsule device 102 is adapted to be split in half after collection of fluid aspirate in order to facilitate movement through lower portions of the GI tract. As shown in FIG. 10A, the outlet conduit 152 extends through the universal mount 148 into the permeable bladder 154. A bladder seal 170 may surround the outlet conduit 152 within the permeable bladder 154. The bladder seal 170 may be disposed to close, such as by a spring, but may be held open by the outlet conduit 152 when the capsule device 102 is not split into two pieces, e.g., in two halves. As shown in FIG. 10B, the capsule device may be split by separating cap 158 from cap 160. The separation of cap 158 and 160 may be controlled by a controller, such as the controller in motor 151, and may occur after fluid aspirate has been collected, for example, at the end of a collection mode or any time after a collection mode has been completed. The splitting of the capsule device 102 may occur as a result of external mechanical forces acting on the capsule device 102 as the capsule device 102 travels through the GI tract. Alternately, any known mechanical mechanism in the art (not herein depicted), such as an actuable clip, may be connected to the motor 151 and used to achieve separation of cap 158 and 160. In some examples, the controller in motor 151 may cause the separation of cap 158 and 160 in response to a sensed change in pH, after a set period of time, or in response to an external control such as a wireless signal received by a wireless receiver. When the cap 158 separates from the cap 160, the outlet conduit is pulled out of the permeable bladder 154, and the bladder seal 170 closes. This protects the collected fluid aspirate from contamination as the permeable bladder 154 is expelled.

Figure 11:
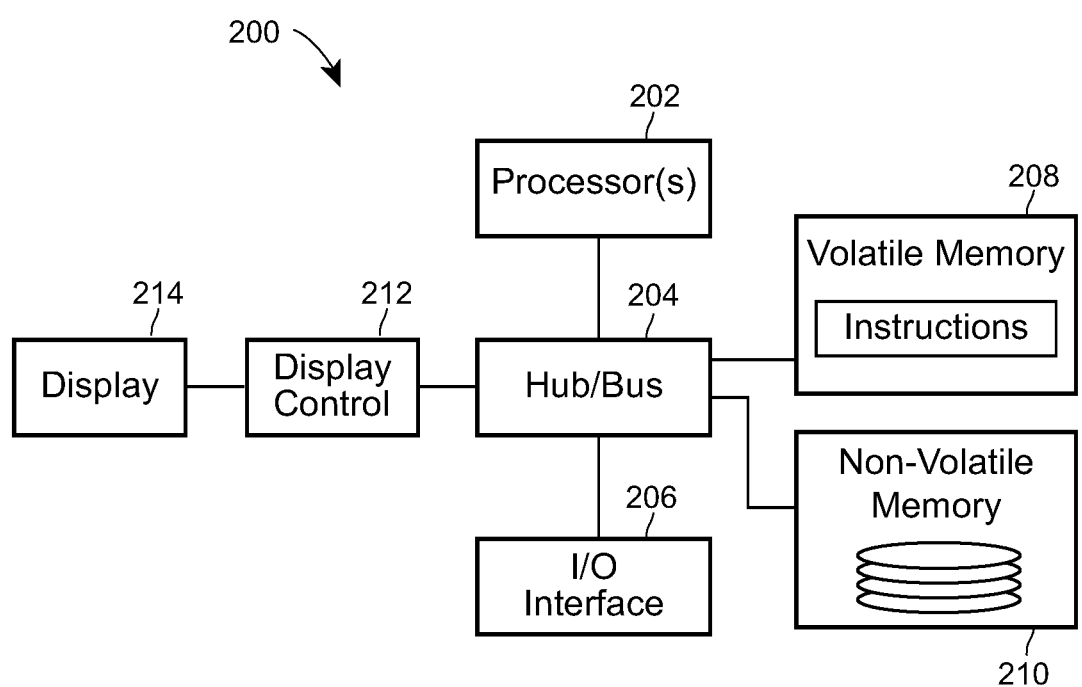
FIG. 11 illustrates a block diagram of a controller for a capsule device of the present disclosure.

FIG. 11 illustrates a block diagram of an example controller 200 (such as controller 12 or the controller associated with motor 141) that may be utilized in a capsule device. The controller 200 may include, for example, one more central processing units (CPUs) or processors 202, and one or more busses or hubs 204 that connect the processor(s) 202 to other elements of the controller 200, such as a volatile memory 208, a non-volatile memory 210, a display controller 212, and an I/O interface 206. The volatile memory 208 and the non-volatile memory 210 may each include one or more non-transitory, tangible computer readable storage media such as random access memory (RAM), read only memory (ROM), FLASH memory, a biological memory, a hard disk drive, a digital versatile disk (DVD) disk drive, etc.).

In an embodiment, the memory 208 and/or the memory 210 may store instructions that are executable by the processor 202. For example, in a capsule device particularly configured to perform the techniques described herein, the instructions may be the instructions executed by the capsule device, such as the processes described herein. The illustrated controller 200 is only one example of a controller suitable to be particularly configured for use in a capsule device. Other embodiments of the controller 200 may also be particularly configured for use in a capsule device, even if the other embodiments have additional, fewer, or alternative components than shown in FIG. 11, have one or more combined components, or have a different configuration or arrangement of the components. Moreover, the various components shown in FIG. 11 can be implemented in hardware, a processor executing software instructions, or a combination of both hardware and a processor executing software instructions, including one or more signal processing and/or application specific integrated circuits.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion.

For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

While the present invention has been described with reference to specific examples, which are intended to be illustrative only and not to be limiting of the invention, it will be apparent to those of ordinary skill in the art that changes, additions and/or deletions may be made to the disclosed embodiments without departing from the spirit and scope of the invention.

The foregoing description is given for clearness of understanding; and no unnecessary limitations should be understood therefrom, as modifications within the scope of the invention may be apparent to those having ordinary skill in the art.

The invention claimed is:

1. An ingestible capsule device comprising:
    a peristaltic pump including an inlet conduit and an outlet conduit;
    a mount connected to the peristaltic pump, the mount including an outlet hole configured to secure the outlet conduit;
    a semi-permeable bladder connected to the mount;
    a non-dissolvable cap surrounding the peristaltic pump, the non-dissolvable cap including an inlet hole; and
    a dissolvable cap surrounding the semi-permeable bladder.

2. The ingestible capsule device of claim 1, wherein the peristaltic pump comprises:
    a stator;
    a cycloid gear configured to engage the stator;
    an eccentric crank connected to a center of the cycloid gear;
    a stator cover configured to cover the stator and cycloid gear;
    an output disk connected to the eccentric crank;
    output pins connected to the output disk;
    rollers connected to the output pins;
    a media tubing secured by the stator cover and in contact with the rollers.

3. The ingestible capsule device of claim 1, wherein the semi-permeable bladder includes an expandable chamber made from an electrospun polymer that is permeable to some fluids.

4. The ingestible capsule device of claim 1, wherein the semi-permeable bladder is expandable within the capsule shell.

5. The ingestible capsule device of claim 1, wherein the semi-permeable bladder has (i) a receiving end adjacent universal mount and configured such that the receiving end is maintained in a fixed position relative to the mount and (ii) a distal end expandable in response to increases in fluid volume in the semi-permeable bladder.

6. The ingestible capsule device of claim 1, wherein the semi-permeable bladder has a maximum volume equal to or greater than one cubic centimeter.

7. The ingestible capsule device of claim 1, wherein the peristaltic pump further includes a motor and motor controller connected to a battery.

8. The ingestible capsule device of claim 7, wherein the motor controller includes a collection mode program that, when activated, operates the peristaltic pump for fluid aspiration.

9. The ingestible capsule device of claim 8, wherein the motor controller includes a timer, and the timer activates the collection mode program.

10. The ingestible capsule device of claim 8, wherein the motor controller is further connected to a sensor disposed on the non-dissolvable cap, and a condition sensed by the sensor activates the collection mode program.

11. The ingestible capsule device of claim 10, wherein the sensor is a pH sensor.

12. The ingestible capsule device of claim 11, wherein the condition sensed by the pH sensor is a pH level between 5.5 and 8.0.

13. The ingestible capsule device of claim 10, wherein the sensor is an impedance sensor.

14. The ingestible capsule device of claim 8, wherein the collection mode program runs for a set period of time.

15. The ingestible capsule device of claim 8, wherein the collection mode program runs multiple times.

16. The ingestible capsule device of claim 15, wherein the multiple times the collection mode program runs are at predetermined intervals.

17. The ingestible capsule device of claim 8, wherein the controller includes a wireless receiver for receiving a wireless signal that activates the controller to start or stop the peristaltic pump from running.

18. The ingestible capsule device of claim 17, further including a remote wireless transmitter for transmitting a wireless signal that activates the controller to either start or stop the peristaltic pump from running.

19. The ingestible capsule device of claim 7, wherein the motor controller includes a sample dispensation mode that, when activated, reverses operation of the peristaltic pump to dispense a collected sample.

20. The ingestible capsule device of claim 2, wherein the media tubing is configured to overlap for a distance, and wherein the peristaltic pump can be sealed by stopping a roller within the distance where the media tubing overlaps.

21. The ingestible capsule device of claim 8, wherein the motor controller monitors draw from the motor and identifies periods when a greater amount of current is drawn and periods when a lesser amount of current is drawn within a cycle of a peristaltic pump, and wherein the collection mode program waits for a period when the greater amount of current is drawn to end the collection mode program.

22. The ingestible capsule device of claim 1, wherein the semi-permeable bladder is configured to be separable from the mount and includes a bladder seal to close the semi-permeable bladder upon removal of the outlet conduit.

* * * * *